United States Patent
Tets et al.

(10) Patent No.: US 10,745,662 B2
(45) Date of Patent: Aug. 18, 2020

(54) NUTRIENT MEDIUM FOR CULTIVATING BACTERIA

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU)

(73) Assignees: Viktor Veniaminovich TETS, St. Petersburg (RU); Georgy Viktorovich TETS, St. Petersburg (RU)

( * ) Notice: Subject to any disclaimer, the term of this patent is extended or adjusted under 35 U.S.C. 154(b) by 285 days.

(21) Appl. No.: 15/739,325

(22) PCT Filed: Jun. 23, 2016

(86) PCT No.: PCT/RU2016/000383
§ 371 (c)(1),
(2) Date: Dec. 22, 2017

(87) PCT Pub. No.: WO2016/209117
PCT Pub. Date: Dec. 29, 2016

(65) Prior Publication Data
US 2019/0382713 A1    Dec. 19, 2019

(30) Foreign Application Priority Data

Jun. 23, 2015  (RU) .................................. 2015124601

(51) Int. Cl.
*C12N 1/20*  (2006.01)
(52) U.S. Cl.
CPC ....................................... *C12N 1/20* (2013.01)
(58) Field of Classification Search
CPC ....................................................... C12N 1/20
See application file for complete search history.

(56) References Cited

U.S. PATENT DOCUMENTS

| | | | |
|---|---|---|---|
| 2,533,088 A | 4/1949 | Brewer et al. | |
| 3,728,461 A | 4/1973 | Douros, Jr. et al. | |
| 5,789,173 A | 8/1998 | Peck et al. | |
| 6,153,400 A | 11/2000 | Matsumura et al. | |
| 6,280,946 B2 | 8/2001 | Hyldig-Nielsen et al. | |
| 6,984,499 B2 | 1/2006 | Chen et al. | |
| 7,262,021 B1 | 8/2007 | Taintor | |
| 8,753,875 B2 | 6/2014 | Frimodt-Moller | |
| 2002/0076742 A1 | 6/2002 | Chen et al. | |
| 2004/0018585 A1 | 1/2004 | Crouteau et al. | |
| 2008/0318268 A1 | 12/2008 | Olson et al. | |
| 2009/0068696 A1 | 3/2009 | Frimodt-Moller | |
| 2009/0310839 A1 | 12/2009 | Katzenelson et al. | |
| 2011/0269130 A1 | 11/2011 | Shi et al. | |
| 2011/0318814 A1 | 12/2011 | Kshirsagar et al. | |
| 2012/0329675 A1 | 12/2012 | Olsen et al. | |
| 2014/0170671 A1 | 6/2014 | McGarr et al. | |
| 2015/0284764 A1 | 10/2015 | Tets et al. | |

FOREIGN PATENT DOCUMENTS

| | | |
|---|---|---|
| BY | 7596 U | 10/2011 |
| CN | 203904353 U | 10/2014 |
| CN | 104313116 A | 1/2015 |
| JP | H1066598 A | 3/1998 |
| RU | 2061032 C1 | 5/1996 |
| RU | 2231554 C2 | 6/2004 |
| RU | 2262533 C2 | 10/2005 |
| RU | 2006111133 A | 10/2007 |
| RU | 69066 U1 | 12/2007 |
| RU | 2319746 C2 | 3/2008 |
| RU | 127749 U1 | 5/2013 |
| RU | 2505813 C1 | 1/2014 |
| WO | 9500112 A1 | 1/1995 |
| WO | 1996/028570 A1 | 9/1996 |
| WO | 1999/018232 A1 | 4/1999 |
| WO | 2004/050675 A1 | 6/2004 |
| WO | 2009/026920 A1 | 3/2009 |

(Continued)

OTHER PUBLICATIONS

Moore, J. Gen. Microbiol., 1968, 53:415-423.*
Balashova, Infection and Immunity, 2006, 74(4):2015-2021.*
Abdou, ARKIVOC, 2007, 45-60.*
Communication issued by the United States Patent and Trademark Office in U.S. Appl. No. 14/439,717, dated Sep. 12, 2017.
Communication issued by the United States Patent and Trademark Office in U.S. Appl. No. 14/439,717, dated Mar. 15, 2018.
Office Action issued by the United States Patent and Trademark Office in U.S. Appl. No. 15/039,966, dated Jun. 5, 2018.
European Communication Pursuant to Article 94(3) EPC issued by the European Patent Office in European Application No. 13 853 343.5, dated May 24, 2018, 5 pages total.
Funk, D.J. et al., "Antimicrobial Therapy for Life-Threatening Infections: Speed is Life" Critical Care Clinics (2011) vol. 27, pp. 53-76.

(Continued)

*Primary Examiner* — Bin Shen
(74) *Attorney, Agent, or Firm* — Troutman Pepper Hamilton Sanders LLP

(57) ABSTRACT

The invention relates to microbiology, and more particularly to nutrient media used for cultivating bacteria for the subsequent study thereof. A nutrient medium comprising a pancreatic digest of casein, a peptic digest of meat, a heart pancreatic digest, yeast extract, starch and water is characterized in that it additionally contains violuric acid and beef infusion, wherein the ratio of ingredients is (wt %): 0.3-1.0 pancreatic digest of casein; 0.1-1.5 peptic digest of meat; 0.1-0.9 heart pancreatic digest; 0.1-2.0 yeast extract, 0.3-0.8 starch; 0.001-0.05 violuric acid; 2.0-15 beef infusion; the remainder water. The nutrient medium can additionally contain 0.3-2.5 wt % agar-agar and/or 1-20 wt % whole or hemolyzed sheep red blood cells and/or 1-20 wt % whole or hemolyzed human red blood cells and/or 1-15 wt % horse blood serum. This provides for the simultaneous growth of the maximum possible number of bacteria present in an inoculate.

10 Claims, No Drawings
Specification includes a Sequence Listing.

(56) References Cited

FOREIGN PATENT DOCUMENTS

| WO | 2011/009213 A1 | 1/2011 |
|---|---|---|
| WO | 2014/074012 A1 | 5/2014 |

OTHER PUBLICATIONS

Hellenkamp, K. et al., "Early Pneumonia and Timing of Antibiotic Therapy in Patients After Nontraumatic Out-of-Hospital Cardiac Arrest" Critical Care (2016) vol. 20, No. 31, 10 pages total.
Birger, M.O., Spravochnik po rnil<robiologichesk.lm i virusologicheskim rnetodam issledovaniya, Ivloskva, Medicina, 1973. pp. 177-178 and English Translation thereof.
Blood Agar, Thermofisher 2008, accessed at: https://tools.thermofisher.com/content/sfs/manuals/IFU1200.pdf.
Dong, Qunfeng et al., "The microbial communities in male first catch urine are highly similar to those in paired urethral swab specimens." PLoS One 6.5 (2011): e19709.
Ellner, P.D. et al., "A New Culture Medium for Medical Bacteriology" The American Journal of Clinical Pathology (1966) vol. 45, No. 4, pp. 502-504.
Epstein S.S., "General model of microbial uncultivability in uncultivated microorganisms", Series: Microbiology Monographs, Springer, 2009, p. 131-150.
European Communication issued by the European Patent Office in European Patent Application No. 13853343.5, dated Nov. 13, 2017, 5 pages total.
European Communication Pursuant to Rules 70(2) and 70a(2) EPC, Extended/Supplementary European Search Report Issued in EP13853343.5, dated Jun. 23, 2016, 7 pages.
European Extended Search Report issued in EP14866121.8, dated Apr. 28, 2018, 9 pages total.
Ghannoum, Mahmoud A. et al., "Characterization of the oral fungal microbiome (mycobiome) in healthy individuals." PLoS pathogens 6.1 (2010): e1000713.
International Preliminary Report on Patentability and Written Opinion (including translation) issued by the International Searching Authority in International Patent Application No. PCT/RU2016/000383, dated Dec. 26, 2017, 9 pages total.
International Preliminary Report on Patentability Issued in PCT/RU2013/000394 dated May 12, 2015, 4 pages and English Translation Thereof.
International Preliminary Report on Patentability Issued in PCT/RU2014/000810 dated May 31, 2016, 5 pages and English Translation Thereof.
International Search Report (including translation) issued by the International Searching Authority in International Patent Application No. PCT/RU2016/000383, dated Oct. 20, 2016, 3 pages total.
International Search Report and Written Opinion Issued in PCT/RU2013/000394 dated Dec. 12, 2013, 11 pages and English Translation Thereof.
International Search Report and Written Opinion issued in PCT/RU2014/000810, dated Jan. 15, 2015, 12 pages and English Translation Thereof.
Isenberg H.D., Essential Procedures for Clinical Microbiology, ASM-PRESS (1998), pp. 208-215, 216-223, and pp. 235-240.
Korotchenko, H.M. et al., "Izuchenie Ustoichivosti Violuratnykh Kompleksov Nekotorykh D-i F-metallov" Zhurnal Neorganicheskoi Khimii (2012) vol. 57, No. 1, pp. 141-147.
Lagace-Wiens, P.R.S. et al., "Treatment of lower urinary tract infection caused by multidrug-resistant extended-spectrum-β-lactamase-producing *Escherichia coli* with amoxicillin/clavulanate: case report and characterization of the isolate" Journal of Antimicrobial Chemotherapy (2006), 57(6):1262-1263.
Lewis K. et al., "Persisters, biofilms, and the problem of culturability in incultivated microorganisms", Series: Microbiology Monographs, Springer, 2009, p. 181-194.
Oliver, J.D., "Recent Findings on the Viable but Nonculturable State in Pathogenic Bacteria" (2010) FEMS Microbiology Reviews (2010) vol. 34, pp. 415-425.
Opredelenie chuvstvitelnosti rnikroorganizmov k antibakterialnym preparatam, metodicheskie rekomendatsii, klinicheskaya Mikrobiologiya Antimikrobnaya Knimioterapiya (2004), vol. 06:04: p. 311-312 and English Translation thereof titled "Determination of the sensitivity of microorganisms to antibiotics".
Petrosino, J.F. et al., "Metagenomic Pyrosequencing and Microbial Identification" Clinical Chemistry (2009) vol. 55, No. 5, pp. 856-866.
Poliak, M.C. et al., "Pitatelnye Sredy Dlia Meditsinskoi Mikrobiologii" St. Petersburg (2002), 80 pages total.
US Food and Drug Administration "Chapter 3: Types of Devices and Predictive Device" in: "Guidance for Industry and for FDA Reviewers Guidance on review Criteria for Assessment of Antiicrobial Susceptibility Devices" (1991), US Department of Health and Human Services, Washington DC USA, XP055364834, pp. 1-22.
Zhou, Xia, et al. "The vaginal bacterial communities of Japanese women resemble those of women in other racial groups," FEMS Immunology & Medical Microbiology 58.2 (201 0): 169-181.
Bhadange, Y. et al., "Role of Liquid Culture Media in the Laboratory Diagnosis of Microbial Keratitis" American Journal of Ophthalmology (2013) vol. 156, No. 4, pp. 745-751.
Database WPI Week 201524 XP002785443, Thomson Scientific (2015) 1 page total.
European Communication (Communication pursuant to Article 94(3) EPC) issued in EP13853343.5, dated Oct. 10, 2018.
European Communication (Extended European Search Report) issued by the European Patent Office in European Patent Application No. 16814798.1, dated Oct. 24, 2018.
Li, L. et al., "The Importance of the Viable but Non-Culturable State in Human Bacterial Pathogens" Frontiers in Microbiology (2014) vol. 5, Article 258, pp. 1-20.

\* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 1
agagtttgat ymtggctcag                                                    20

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
attaccgcgg ctgctgg                                                       17
```

NUTRIENT MEDIUM FOR CULTIVATING BACTERIA

CROSS-REFERENCE TO RELATED APPLICATIONS

This application is a U.S. National Phase Application under 35 U.S.C. § 371 of International Patent Application No. PCT/RU2016/000383, filed Jun. 23, 2016, which published as WO 2016/209117 A1 on Dec. 29, 2016 and which claims priority to Russian Patent Application No. 2015124601, filed on Jun. 23, 2015, all of which are herein incorporated by reference in their entirety.

SEQUENCE LISTING

The instant application contains a Sequence Listing which has been filed electronically in ASCII format and is hereby incorporated by reference in its entirety. Said ASCII copy, created on Feb. 6, 2020, is named 244008_000068_SL.txt and is 813 bytes in size.

TECHNICAL FIELD

The invention relates to microbiology, and more particularly to nutrient media used for cultivating bacteria for the subsequent study thereof.

BACKGROUND ART

For the growth and multiplication process, the bacteria must receive all the substances that are necessary for the biosynthesis of cellular components and energy production [Balows A., Hausler W. J. Jr., Herrmann K. L., Isenberg H. D., Shadow H. J. Manual of clinical Microbiology, 5thed. ASM, 1991, 1226-1288].

Nutrient media are divided into media of general use suitable for the generation of many species of microorganisms, and special media, designed for selective cultivation of certain types of bacteria, studying of their properties and storage. Among the special media are elective (selective), differential-diagnostic (indicator) and canning [Balows A., Hausler W. J. Jr., Herrmann K. L., Isenberg H. D., Shadow H. J. Manual of clinical Microbiology, 5thed. ASM, 1991, 1226-1288].

There is a general-purpose medium, the so-called Columbian medium, containing pancreatic digest of casein, pepsin digest of meat, pancreatic digest of a heart, yeast extract, starch and water.

This medium was chosen by us as a prototype of the claimed invention [Ellner, P D, C J Stoessel, E. Drakeford, and F. Vasi. 1966. A new culture medium for medical bacteriology. Am. J. Clin. Pathol. 45:502-504].

The disadvantage of the prototype is the fact that its use does not take into account the two qualities of the medium, the need for which arose after the discovery of the bacteria called "not yet cultivated" [Oliver, J D. "Recent findings on the viable but nonculturable state in pathogenic bacteria." FEMS Microbiol Rev 2010, 34: 415-25]—the simultaneous growth in a single casserole (tube) of a mixture of maximally diverse bacteria and a sufficient rate of growth of both individual bacteria and their mixed communities.

SUMMARY OF THE INVENTION

It is an object of the present invention to provide a nutrient medium allowing simultaneous growth of the maximum possible number of bacteria present in the seed material.

According to the invention, the nutrient medium including pancreatic digest of casein, pepsin digest of meat, pancreatic digest of a heart, yeast extract, starch and water, additionally contains violuric acid and beef infusion, with the following ratio of components (wt %):

pancreatic digest of casein—0.3-1.0;
pepsin digest of meat—0.1-1.5;
pancreatic digest of a heart—0.1-0.9;
yeast extract 0.1-2.0;
starch—0.3-0.8;
violuric acid—0.001-0.05;
infusion of beef—2.0-15;
water—the rest.

The nutrient medium may additionally contain 0.3 to 2.5 wt % of agar-agar and/or whole or hemolysed erythrocytes of sheep blood—1-20 wt %, and/or whole hemolyzed erythrocytes of human blood—1-20 wt %, and/or horse blood serum—1-15% by weight.

The applicant is not aware of any sources of information that would contain information about identical technical solutions, which makes it possible to conclude that the claimed invention complies with the "Novelty" ("N") criterion.

Due to the implementation of the claimed technical solution, a technical result is achieved, which is to ensure a sufficient simultaneous growth of the maximum possible number of bacteria present in the material being sown.

The applicant has not found any sources of information containing data on the influence of the features of the invention on the technical result produced by the invention.

In applicant's opinion, the abovementioned new properties of the object enable to conclude that the invention conforms to the criterion "Inventive Step" (IS).

PREFERRED EMBODIMENT

Preparation of Nutrient Medium

The medium was prepared as follows: the following weighed portions of the medium components were prepared, wt %: pancreatic digest of casein, 0.3-1.0; pepsin digest of meat, 0.1-1.5; pancreatic digest of a heart, 0.1-0.9; yeast extract, 0.1-2.0; starch, 0.3-0.8; violuric acid, 0.001-0.05; beef infusion, 2.0-15. The components were mixed, distilled water was added to a total volume of 1000 ml, a pH of 7.3±0.2 was set (a 0.1 N hydrochloric acid solution or 0.1 N sodium hydroxide solution) and boiled, then hot-filtered through a paper, cotton-gauze, or other type of filter, or a web that retains mechanical impurities, or allowed to stand.

To prepare the agar medium 0.3-2.5 wt % agar-agar was added to the original mixture before adding water, after which the preparation was carried out in the same way as for the liquid medium. The settled melted agar media were filtered through a cotton-gauze filter.

The medium was sterilized by high temperature in autoclaves under pressure or with flowable steam. Typically, the medium was sterilized in an autoclave at 0.5-1.0 atm. (120.6°) for 15-30 minutes. After cooling to +450° C., whole or hemolyzed erythrocytes of ram blood or human blood 1-20 wt %, or horse blood serum (1-15 wt %) were added to the medium according to the example.

Assessment of Microbial Diversity

An artificial mixture of bacteria with morphological features distinguishable by light microscopy was placed on the medium: gram-positive representatives of the genera

*Staphylococcus, Streptococcus, Micrococcus,* various *Corynebacterium,* spore-forming *Bacillus, Paenibacillus, Oceanobacillus,* various *Actinomyces, Lactobacillus* Gram-negative *Neisseria, Escherichia, Brucella, Pseudomonas, Acinetobacter, Proteus, Bordetella.* From the colonies of microorganisms smears were prepared and then Gram stained, followed by the use of light microscopy.

The results of the comparison with the prototype of the claimed nutrient medium and medium supplemented with agar-agar according to the number of different grown bacteria are given in Table 1.

Analysis of the results shown in Table 1 showed that the declared nutrient medium with the addition of agar-agar and without it allows the cultivation of a maximum number of microorganisms superior to that of the prototype, both with the addition of erythrocytes of the blood of a ram or human blood or serum and without them.

The results of the comparison with the prototype according to the number of different grown bacteria are given in Table 2.

Analysis of the results shown in Table 2 showed that the declared liquid nutrient medium allows the cultivation of a maximum number of microorganisms superior to that of the prototype, both with the addition of erythrocytes of the blood of a ram or human blood or serum and without them.

Bacteria Growth Rate

In addition, a comparison with the prototype of the composition of the components as of Example 12 of the claimed nutrient medium with respect to the growth time of the grown colonies of microorganisms was performed on a liquid nutrient medium with the composition of the components in accordance with Examples 14, 15, 18, 19, 22, and 23. In the medium, 10 strains of various bacteria were sown (the mixture included various strains of staphylococci, *Escherichia coli,* microcroc, *corynebacterium, salmonella, pseudomonas, proteus,* bacilli). The results of the comparison with the prototype according to the growth time of the grown colonies of microorganisms are given in Table 3.

Analysis of the results shown in Table 3 showed that the declared nutrient medium allows obtaining the maximum variety of microorganisms in the material under study, after 8 hours of growth, while on the prototype medium the appearance of the maximum number of morphotypes was recorded only after 12 hours of growth.

Efficacy of Using a Nutrient Medium to Extract Bacteria from a Pathological Material The tested material was sown on a nutrient medium with the composition of the components as in Examples 2-11, 13-23. As a comparison, a medium selected as a prototype with the composition of the components as of Example 12 was used. The samples were incubated at 37° C. for 24 hours.

Metagenomic Analysis

Extraction of DNA.

DNA extraction from the pathological material and bacteria grown on the medium was carried out using a standard QIAamp DNA Mini Kit (QIAGEN) according to the available protocol.

Amplification was performed using eubacterial primers 27F-534R flanking the hypervariable region of the 16S rRNA gene.

27F:
'5-AGAGTTTGATYMTGGCTCAG-3'

534R:
'5-ATTACCGCGGCTGCTGG-3'.

The pair of oligonucleotide primers used in the work is specific to the conserved sections of the 16S rRNA gene and is used in metagenomic studies to detect the bacterial diversity of various communities [Dong, Qunfeng, et al. "The microbial communities in male first catch urine are highly similar to those in paired urethral swab specimens." PLoS One 6.5 (2011): e19709. Petrosino, Joseph F., et al. "Metagenomic pyrosequencing and microbial identification." Clinical Chemistry 55.5 (2009): 856-866].

Metagenomic sequencing of the fragment of the 16S rRNA gene was performed on a Roche/454 Genome Sequencer FLX Titanium pyrosequencer. The maximum length of the sequences obtained was 507 nucleotides; chimeric sequences and sequences shorter than 300 nucleotides were not included in the analysis.

Analysis of Diversity and Taxonomic Composition

Each sequence obtained during pyrosequencing was identified by comparison with the sequences of the GenBank and EzTaxon databases using the BLASTN search algorithms and pairwise comparison. To determine the species diversity, the taxonomic composition and for comparison of communities, the Pyrosequencing pipeline (http://pyro.cme.ms-u.edu) was used. The resulting sequences were aligned and cluster analysis was performed using the Complete Linkage Clustering program, which is part of the Pyrosequencing pipeline. Clustering was performed at different levels characterized by different distances between clusters (from 0 to 0.25 in 0.01 increments). The isolation of the filotypes (OTU) was carried out at a cluster distance of 0.03; assessment of the taxonomic complexity of communities was carried out at levels of differences corresponding to the following taxa: species—0.03, genus—0.05, family—0.1, using Rarefaction program (Pyrosequencing pipeline). To characterize the taxonomic composition of communities, a cluster analysis was carried out. Next, the same was carried out for each cluster, by means of Dereplicate Request program for the nucleotide sequence corresponding to the cluster center having the minimum sum of squares of distances to the other sequences in the cluster. Representative cluster sequences were taxonomically classified. Classification of species at all stages of work was carried out on the basis of the genotypic approach in accordance with the international code of the nomenclature of bacteria (ICNB). If the representative sequence had a homology of more than 97% with the sequence of the validated microorganism, the cluster was assigned to the corresponding species.

Bacteria in Urine

As a result of pyrosequencing, a significant species diversity of bacteria was found in the urine sample, where one order, one family, and four Enterobacteriales species were detected. In the pathological material, microorganisms of four genera of the Enterobacteriales order were found. The species of microorganisms occurring in the urine isolated on a nutrient medium with the composition of the components according to Examples 2-11, 13-23, are shown in Table 4.

On the medium selected as a prototype with the composition of the components according to Examples 1 and 12, the growth of bacteria of only one species identified as *Escherichia coli* was obtained.

While on the declared nutrient medium with the composition of the components in all the examples as a result of the studies almost 100% coincidence of the microorganism species giving growth on the declared medium in comparison with the urine species was obtained from the metagenomic analysis, which indicates a high efficiency of the claimed nutrient medium to ensure the growth of the entire diversity of bacteria that occur in the pathological material of the type being studied.

Bacteria in Traumatic Discharge

As a result of pyrosequencing, a significant species diversity of bacteria was found in the traumatic detachable, which includes bacteria belonging to one order, one family, and 8 species. In the pathological material, the number of sequences was dominated by bacteria of the order of Enterobacteriales. The species of microorganisms occurring in the traumatic detachable isolated on a nutrient medium with the composition of the components according to Examples 2-11, 13-23, are shown in Table 5.

On the medium selected as a prototype with the composition of the components according to Examples 1 and 12, the growth of bacteria of only one species identified as *Klebsiella oxytoca* was obtained.

While on the declared nutrient medium with the composition of the components in all the examples as a result of the studies almost 100% coincidence of the microorganism species giving growth on the declared medium in comparison with the traumatic discharge species was obtained from the metagenomic analysis, which indicates a high efficiency of the claimed nutrient medium to ensure the growth of the entire diversity of bacteria that occur in the pathological material of the type being studied.

Detection of a large number of bacteria of different species of the same genus during metagenomic analysis indicates the presence of bacteria with an unexplored genome, i.e. related to the group of unknown, yet not cultivated bacteria.

Bacteria in Sputum

As a result of pyrosequencing, a significant species diversity of bacteria in sputum was detected, which includes the following microorganisms: 7 orders, 8 families, 15 species. In the pathological material, the number of sequences was dominated by bacteria of the two orders: Pseudomonadales and Burkholderiales. In the sputum the representation of Pseudomonadales and Burkholderiales was 88.3% and 8.5%. Isolated on a nutrient medium with the composition of the components according to Examples 2-11, 13-23, the species of microorganisms occurring in the sputum are shown in Table 6.

On the medium selected as a prototype with the composition of the components according to Examples 1 and 12, the growth of bacteria of only one species identified as *Staphylococcus epidermidis* was obtained.

While on the declared nutrient medium with the composition of the components in all the examples as a result of the studies almost 100% coincidence of the microorganism species giving growth on the declared medium in comparison with the sputum species was obtained from the metagenomic analysis, which indicates a high efficiency of the claimed nutrient medium to ensure the growth of the entire diversity of bacteria that occur in the pathological material of the type being studied.

INDUSTRIAL APPLICABILITY

The invention can be implemented using common constructional materials and equipment, resulting, according to the applicant's opinion, in compliance of the invention with the "Industrial Applicability" ("IA") patentability criterion.

Embodiments

1. The nutrient media for cultivating bacteria including pancreatic digest of casein, pepsin digest of meat, pancreatic digest of a heart, yeast extract, starch and water, characterized in that it additionally contains violuric acid and beef infusion, with the following ratio of components (wt %):
    pancreatic digest of casein—0.3-1.0;
    pepsin digest of meat—0.1-1.5;
    pancreatic digest of a heart—0.1-0.9;
    yeast extract—0.1-2.0;
    starch—0.3-0.8;
    infusion of beef—2.0-15;
    violuric acid—0.001-0.05;
    water—the rest.
2. The nutrient medium according to embodiment 1, characterized in that it additionally contains agar-agar (0.3-2.5 wt %).
3. The nutrient medium according to embodiment 1 or 2, characterized in that it additionally contains horse blood serum—1-15 wt %. 4. The nutrient medium according to embodiment 1 or 2, characterized in that it additionally contains erythrocytes of ram blood—1-20 wt %.
5. The nutrient medium according to embodiment 4 characterized in that it additionally contains hemolyzed erythrocytes of ram blood—1-20 wt %.
6. The nutrient medium according to embodiment 1 or 2, characterized in that it additionally contains erythrocytes of human blood—1-20 wt %.
7. The nutrient medium according to embodiment 6 characterized in that it additionally contains hemolyzed erythrocytes of human blood—1-20 wt %.

TABLE 1

Number of different bacteria grown on claimed nutrient media supplemented with agar-agar

| # Example 1 | Nutrient media. Mass % 2 | Number of different bacteria in the artificial mixture 3 | Number of different bacteria grown on nutrient medium 4 |
|---|---|---|---|
| 1 | Prototype: pancreatic casein digest - 0.5 | 25 | 10 |

TABLE 1-continued

Number of different bacteria grown on claimed
nutrient media supplemented with agar-agar

| # Example 1 | Nutrient media. Mass % 2 | Number of different bacteria in the artificial mixture 3 | Number of different bacteria grown on nutrient medium 4 |
|---|---|---|---|
| | pepsin meat digest -1<br>heart pancreatic digest - 0.5<br>yeast extract -0.15<br>starch - 0.5<br>water - 97.35 | | |
| 2 | Media according to embodiment 1:<br>pancreatic casein digest - 0.3<br>pepsin meat digest-0.1<br>heart pancreatic digest - 0.1<br>yeast extract - 0.1<br>starch 0.3<br>vialuric acid - 0.001<br>beef tincture - 2.0<br>water - 97.099 | 25 | 14 |
| 3 | Media according to embodiment 2:<br>pancreatic casein digest - 1.0<br>pepsin meat digest - 1.5<br>heart pancreatic digest - 0.9<br>yeast extract - 2.0<br>starch - 0.8<br>vialuric acid - 0.05<br>beef tincture - 15.0<br>agar-agar - 0.3<br>water - 78.45 | 25 | 17 |
| 4 | Media according to embodiment 3:<br>pancreatic casein digest - 0.5<br>pepsin meat digest - 0.5<br>heart pancreatic digest - 0.5<br>yeast extract - 0.5<br>starch - 0.5<br>vialuric acid - 0.01<br>beef tincture - 8.0<br>agar-agar - 0.8<br>horse serum - 5.0<br>water - 83.69 | 25 | 21 |
| 5 | Media according to embodiment 3:<br>pancreatic casein digest - 0.8<br>pepsin meat digest-1.2<br>heart pancreatic digest - 0.8<br>yeast extract - 1.5<br>starch - 0.8<br>vialuric acid - 0.04<br>beef tincture - 12.0<br>agar-agar - 2.2<br>horse serum - 15.0<br>water - 65.66 | 25 | 22 |
| 6 | Media according to embodiment 4:<br>pancreatic casein digest - 0.9<br>pepsin meat digest 1.0<br>heart pancreatic digest - 0.7<br>yeast extract - 1.0<br>starch - 0.6<br>vialuric acid - 0.04<br>beef tincture - 10.0<br>agar-agar - 1.2<br>non-hemolyzed lamb - erythrocytes - 1.0<br>water - 83.56 | 25 | 21 |
| 7 | Media according to embodiment 5:<br>pancreatic casein digest - 0.6<br>pepsin meat digest - 0.8<br>heart pancreatic digest - 0.4<br>yeast extract - 0.7<br>starch - 0.4<br>vialuric acid - 0.03<br>beef tincture - 7.0<br>agar-agar - 0.9<br>hemolyzed lamb erythrocytes - 5.0<br>water - 84.17 | 25 | 21 |
| 8 | Media according to embodiment 5:<br>pancreatic casein digest - 0.6<br>pepsin meat digest - 0.8 | 25 | 22 |

TABLE 1-continued

Number of different bacteria grown on claimed nutrient media supplemented with agar-agar

| # Example 1 | Nutrient media. Mass % 2 | Number of different bacteria in the artificial mixture 3 | Number of different bacteria grown on nutrient medium 4 |
|---|---|---|---|
|  | heart pancreatic digest - 0.4<br>yeast extract - 0.7<br>starch - 0.4<br>vialuric acid - 0.03<br>beef tincture - 7.0<br>agar-agar - 0.9<br>hemolyzed lamb erythrocytes - 20.0<br>water - 69.17 |  |  |
| 9 | Media according to embodiment 6:<br>pancreatic casein digest - 0.9<br>pepsin meat digest- 1.0<br>heart pancreatic digest - 0.7<br>yeast extract - 1.0<br>starch - 0.6<br>vialuric acid - 0.04<br>beef tincture - 10.0<br>agar-agar - 1.2<br>non-hemolyzed human erythrocytes - 1.0<br>water - 83.56 | 25 | 20 |
| 10 | Media according to embodiment 7:<br>pancreatic casein digest - 0.6<br>pepsin meat digest - 0.8<br>heart pancreatic digest - 0.4<br>yeast extract - 0.7<br>starch - 0.4<br>vialuric acid -0.03<br>beef tincture - 7.0<br>agar-agar - 0.9<br>hemolyzed human erythrocytes - 5.0<br>water - 84.17 | 25 | 21 |
| 11 | Media according to embodiment 7:<br>pancreatic casein digest - 0.6<br>pepsin meat digest- 0.8<br>heart pancreatic digest - 0.4<br>yeast extract - 0.7<br>starch - 0.4<br>vialuric acid - 0.03<br>beef tincture - 7.0<br>agar-agar - 0.9<br>hemolyzed human erythrocytes - 20.0<br>water - 69.17 | 25 | 22 |

TABLE 2

Number of different bacteria grown on claimed liquid nutrient media

| # Example 1 | Nutrient media. Mass % 2 | Number of different bacteria in the artificial mixture 3 | Number of different bacteria grown on nutrient medium 4 |
|---|---|---|---|
| 12 | Prototype:<br>pancreatic casein digest - 1.0<br>pepsin meat digest - 1.4<br>heart pancreatic digest - 0.9<br>yeast extract - 1.5<br>starch - 0.8<br>water - 94.4 | 12 | 7 |
| 13 | Media according to embodiment 1:<br>pancreatic casein digest - 1.0<br>pepsin meat digest- 1.5<br>heart pancreatic digest - 0.9<br>yeast extract - 2.0<br>starch - 0.8<br>vialuric acid - 0.05<br>beef tincture - 15.0<br>water - 78.75 | 12 | 9 |

TABLE 2-continued

Number of different bacteria grown on claimed liquid nutrient media

| # Example 1 | Nutrient media. Mass % 2 | Number of different bacteria in the artificial mixture 3 | Number of different bacteria grown on nutrient medium 4 |
|---|---|---|---|
| 14 | Media according to embodiment 3:<br>pancreatic casein digest - 0.5<br>pepsin meat digest - 0.5<br>heart pancreatic digest - 0.5<br>yeast extract - 0.5<br>starch - 0.5<br>vialuric acid - 0.01<br>beef tincture - 8.0<br>horse serum - 1.0<br>water - 88.49 | 12 | 10 |
| 15 | Media according to embodiment 3:<br>pancreatic casein digest - 0.5<br>pepsin meat digest - 0.5<br>heart pancreatic digest - 0.5<br>yeast extract - 0.5<br>starch - 0.5<br>vialuric acid - 0.01<br>beef tincture - 8.0<br>horse serum - 5.0<br>water - 84.49 | 12 | 10 |
| 16 | Media according to embodiment 4:<br>pancreatic casein digest - 0.9<br>pepsin meat digest - 1.0<br>heart pancreatic digest - 0.7<br>yeast extract - 1.0<br>starch - 0.6<br>vialuric acid - 0.04<br>beef tincture 10.0<br>non-hemolyzed lamb erythrocytes - 5.0<br>water - 80.76 | 12 | 10 |
| 17 | Media according to embodiment 4:<br>pancreatic casein digest - 0.4<br>pepsin meat digest- 0.8<br>heart pancreatic digest - 0.2<br>yeast extract - 0.8<br>starch - 0.4<br>vialuric acid - 0.04<br>beef tincture - 5.0<br>non-hemolyzed lamb erythrocytes - 20.0<br>water - 72.36 | 12 | 10 |
| 18 | Media according to embodiment 5:<br>pancreatic casein digest - 0.9<br>pepsin meat digest - 1.2<br>heart pancreatic digest - 0.7<br>yeast extract - 1.7<br>starch - 0.7<br>vialuric acid - 0.04<br>beef tincture - 12.0<br>hemolyzed lamb erythrocytes - 1.0<br>water - 81.76 | 12 | 10 |
| 19 | Media according to embodiment 5:<br>pancreatic casein digest - 0.6<br>pepsin meat digest - 0.8<br>heart pancreatic digest - 0.4<br>yeast extract - 0.7<br>starch - 0.4<br>vialuric acid 0.03<br>beef tincture - 7.0<br>hemolyzed lamb erythrocytes - 10.0<br>water - 80.07 | 12 | 10 |
| 20 | Media according to embodiment 6:<br>pancreatic casein digest - 0.9<br>pepsin meat digest - 1.0<br>heart pancreatic digest - 0.7<br>yeast extract - 1.0<br>starch - 0.6<br>vialuric acid - 0.04<br>beef tincture - 10.0<br>non-hemolyzed human erythrocytes - 5.0<br>water - 80.76 | 12 | 10 |

TABLE 2-continued

Number of different bacteria grown on claimed liquid nutrient media

| # Example 1 | Nutrient media. Mass % 2 | Number of different bacteria in the artificial mixture 3 | Number of different bacteria grown on nutrient medium 4 |
|---|---|---|---|
| 21 | Media according to embodiment 6:<br>pancreatic casein digest - 0.4<br>pepsin meat digest - 0.8<br>heart pancreatic digest - 0.2<br>yeast extract - 0.8<br>starch - 0.4<br>vialuric acid - 0.04<br>beef tincture - 5.0<br>non-hemolyzed human erythrocytes - 20.0<br>water - 72.36 | 12 | 10 |
| 22 | Media according to embodiment 7:<br>pancreatic casein digest - 0.9<br>pepsin meat digest 1.2<br>heart pancreatic digest - 0.7<br>yeast extract - 1.7<br>starch - 0.7<br>vialuric acid - 0.04<br>beef tincture - 12.0<br>hemolyzed human erythrocytes - 1.0<br>water - 81.76 | 12 | 10 |
| 23 | Media according to embodiment 7:<br>pancreatic casein digest - 0.6<br>pepsin meat digest - 0.8<br>heart pancreatic digest - 0.4<br>yeast extract - 0.7<br>starch - 0.4<br>vialuric acid - 0.03<br>beef tincture - 7.0<br>hemolyzed human erythrocytes -10.0<br>water - 80.07 | 12 | 10 |

TABLE 3

Number of different morphotypes of grown colonies of microorganisms at different time-points

| Nutrient media # example | Number of identified morphotypes of grown colonies of microorganisms Time of growth (hours) | | | | | | |
|---|---|---|---|---|---|---|---|
| | 2 | 4 | 6 | 8 | 12 | 18 | 24 |
| 1 | 2 | 3 | 4 | 5 | 6 | 7 | 8 |
| Prototype: Example 12 | 0 | 2 | 4 | 6 | 7 | 7 | 7 |
| Media according to embodiment 3:<br>Example 14 | 0 | 4 | 8 | 10 | 10 | 10 | 10 |
| Media according to embodiment 5 or 7:<br>Example 18 or 22 | 0 | 4 | 8 | 10 | 10 | 10 | 10 |
| Media according to embodiment 3:<br>Example 15 | 0 | 6 | 8 | 10 | 10 | 10 | 10 |
| Media according to embodiment 5 or 7:<br>Example 19 or 23 | 0 | 6 | 8 | 10 | 10 | 10 | 10 |

TABLE 4

Isolated bacteria that could be found in urine

| Classification | Pathological material, urine | Claimed nutrient media | Prototype |
|---|---|---|---|
| Order | Enterobacteriales | Enterobacteriales | Enterobacteriales |
| Family | Enterobacteriaceae | Enterobacteriaceae | Enterobacteriaceae |
| Species | *Escherichia coli*<br>*Shigella* spp<br>*Enterbacter cloacae*<br>*Enterobacter hormaechei* | *Escherichia coli*<br>*Shigella* spp<br>*Enterbacter cloacae*<br>*Enterobacter hormaechei* | *Escherichia coli* |

TABLE 5

Isolated bacteria that could be found in wound exudate (wound fluid)

| Classification | Pathological material, wound exudate (wound fluid) | Claimed nutrient media | Prototype |
|---|---|---|---|
| Order | Enterobacteriales | Enterobacteriales | Enterobacteriales |
| Family | Enterobacteriaceae | Enterobacteriaceae | Enterobacteriaceae |
| Species | Enterobacter aerogens | Enterobacter aerogens | Klebsiella oxytoca |
| | Enterobacter asburiae | Enterobacter asburiae | |
| | Enterobacter cancerogenus | Enterobacter cancerogenus | |
| | Enterobacter cloacae | Enterobacter cloacae | |
| | Enterobacter hormaechei | Enterobacter hormaechei | |
| | Klebsiella oxytoca | Klebsiella oxytoca | |
| | Klebsiella pneumoniae | Klebsiella pneumoniae | |
| | Pantoea aggloerans | Pantoea aggloerans | |

TABLE 6

Isolated bacteria that could be found in mucous

| Classification 1 | Pathological material, mucous 2 | Claimed nutrient media 3 | Prototype 4 |
|---|---|---|---|
| Order | Bacillales | Bacillales | Bacillales |
| | Pseudomonales | Pseudomonales | |
| | Clostridiales | Clostridiales | |
| | Actinomycetales | Actinomycetales | |
| | Lactobacillales | Lactobacillales | |
| | Burkholderiales | Burkholderiales | |
| | Sphingomonadales | Sphingomonadales | |
| Family | Staphylococcaceae | Staphylococcaceae | Staphylococcaceae |
| | Corynebacteriuaceae | Corynebacteriuaceae | |
| | Streptococcaceae | Streptococcaceae | |
| | Pseudomonadaceae | Pseudomonadaceae | |
| | Alcaligenaceae | Alcaligenaceae | |
| | Carnobacteriaceae | Carnobacteriaceae | |
| | Sphingomonadaceae | Sphingomonadaceae | |
| | Oxalobacteraceae | Oxalobacteraceae | |
| Species | Staphylococcus epidermididis | Staphylococcus epidermididis | Staphylococcus epidermididis |
| | Lactobacillus rhamnosus | Lactobacillus rhamnosus | |
| | Pseudomonas sp | Pseudomonas sp | |
| | Pseudomonas aeruginosa | Pseudomonas aeruginosa | |
| | Achromobacter insolitus | Achromobacter insolitus | |
| | Achromobacter xylosoxidans | Achromobacter xylosoxidans | |
| | Achromobacter sp | Achromobacter sp | |
| | Granulicatella adiacens | Granulicatella adiacens | |
| | Sphingomonas sp | Sphingomonas sp | |
| | Streptococcus sp | Streptococcus sp | |
| | Hebaspirillum sp | Hebaspirillum sp | |
| | Corynebacterium striatum | Corynebacterium striatum | |
| | Granulicatella adiacens | Granulicatella adiacens | |
| | Achromobacter denitrificans | Achromobacter denitrificans | |

The invention claimed is:

1. A nutrient media for cultivating bacteria comprising a pancreatic digest of casein, pepsin digest of meat, pancreatic digest of a heart, yeast extract, starch, water, violuric acid, beef infusion, in the following ratio of components:
   0.3-1.0 wt % pancreatic digest of casein;
   0.1-1.5 wt % pepsin digest of meat;
   0.1-0.9 wt % pancreatic digest of a heart;
   0.1-2.0 wt % yeast extract;
   0.3-0.8 wt % starch;
   2.0-15 wt % infusion of beef;
   0.001-0.05 wt % violuric acid; and
   water—the rest.

2. The nutrient medium according to claim 1, further comprising 0.3-2.5 wt % agar-agar.

3. The nutrient medium according to claim 2, further comprising 1-15 wt % horse blood serum.

4. The nutrient medium according to claim 2, further comprising 1-20 wt % erythrocytes of ram blood.

5. The nutrient medium according to claim 2 further comprising 1-20 wt % erythrocytes of human blood.

6. The nutrient medium according to claim 1, further comprising 1-15 wt % horse blood serum.

7. The nutrient medium according to claim 1, further comprising 1-20 wt % erythrocytes of ram blood.

8. The nutrient medium according to claim 7, further comprising 1-20 wt % hemolyzed erythrocytes of ram blood.

9. The nutrient medium according to claim 1, further comprising 1-20 wt % erythrocytes of human blood.

10. The nutrient medium according to claim 9, further comprising 1-20 wt % hemolyzed erythrocytes of human blood.

* * * * *